United States Patent [19]

Silver et al.

[11] Patent Number: 5,009,645

[45] Date of Patent: Apr. 23, 1991

[54] SYRINGE FOR DISPENSING MEASURED QUANTITIES OF A MATERIAL

[76] Inventors: Jules Silver, 7 Ridgewood Rd., Niantic, Conn. 06357; Richard A. Tarozzi, 8 Oakwood Dr., Gales Ferry, Conn. 06335

[21] Appl. No.: 365,285

[22] Filed: Jun. 12, 1989

[51] Int. Cl.$^5$ ............................................. A61M 5/00
[52] U.S. Cl. .................................. 604/207; 604/210
[58] Field of Search ............... 604/207, 208, 209, 210, 604/218, 220, 187

[56] References Cited

U.S. PATENT DOCUMENTS 4,711,637 12/1987 Leigh et al. ...................... 604/220

Primary Examiner—John D. Yasko
Attorney, Agent, or Firm—Paul Burd

[57] ABSTRACT

A disposable syringe for dispensing a metered dosage of a material includes a plunger rod which is axially movable within a syringe barrel for dispensing the material. The plunger rod includes a rail section located axially outside the syringe barrel, and a slidable stop member is secured to the rail section for adjusting the volume of material to be dispensed. The adjustable stop member includes a knife edge for embedding into a surface of the rail section of the plunger rod to lock the stop member in a desired position.

19 Claims, 3 Drawing Sheets

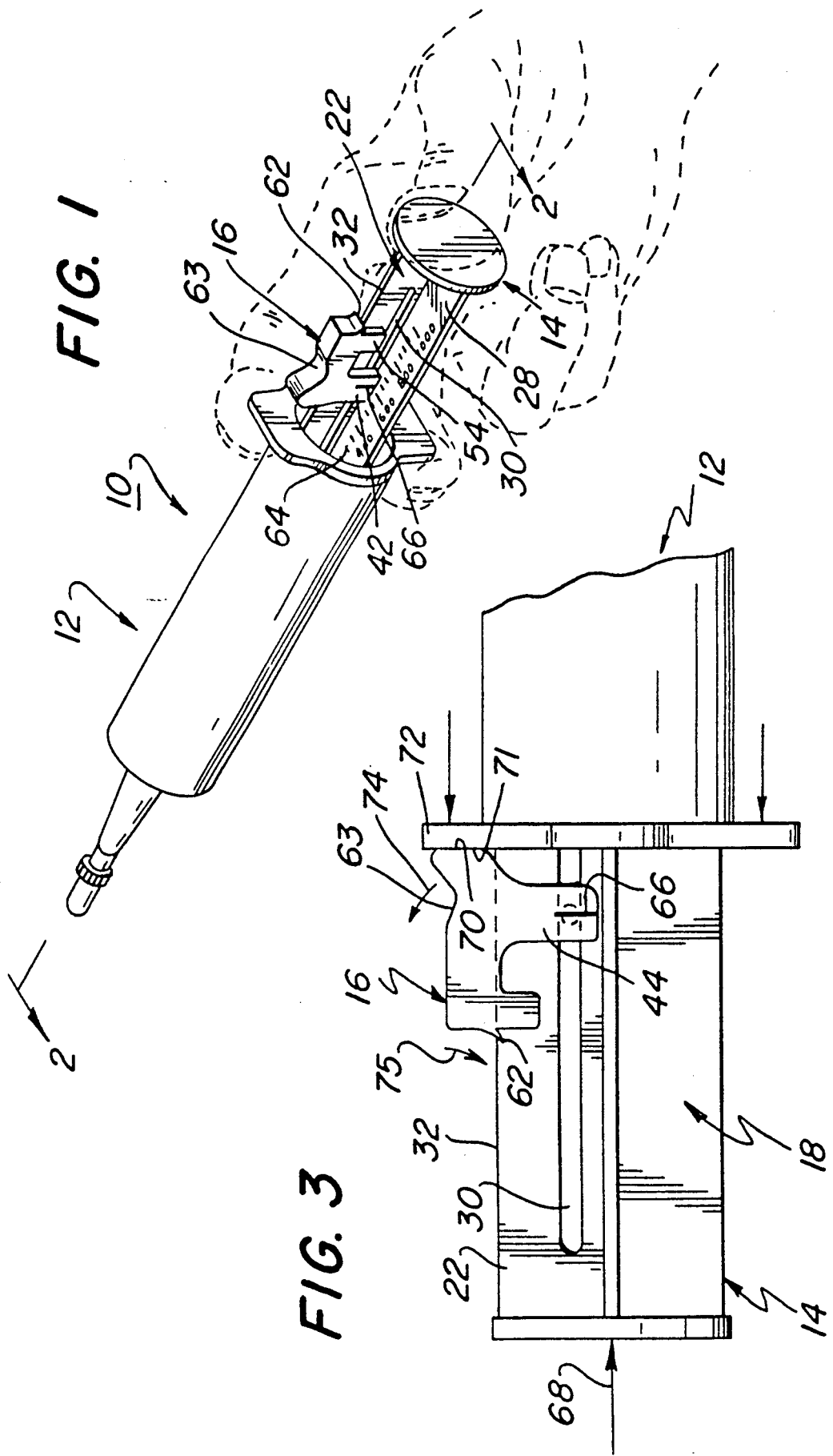

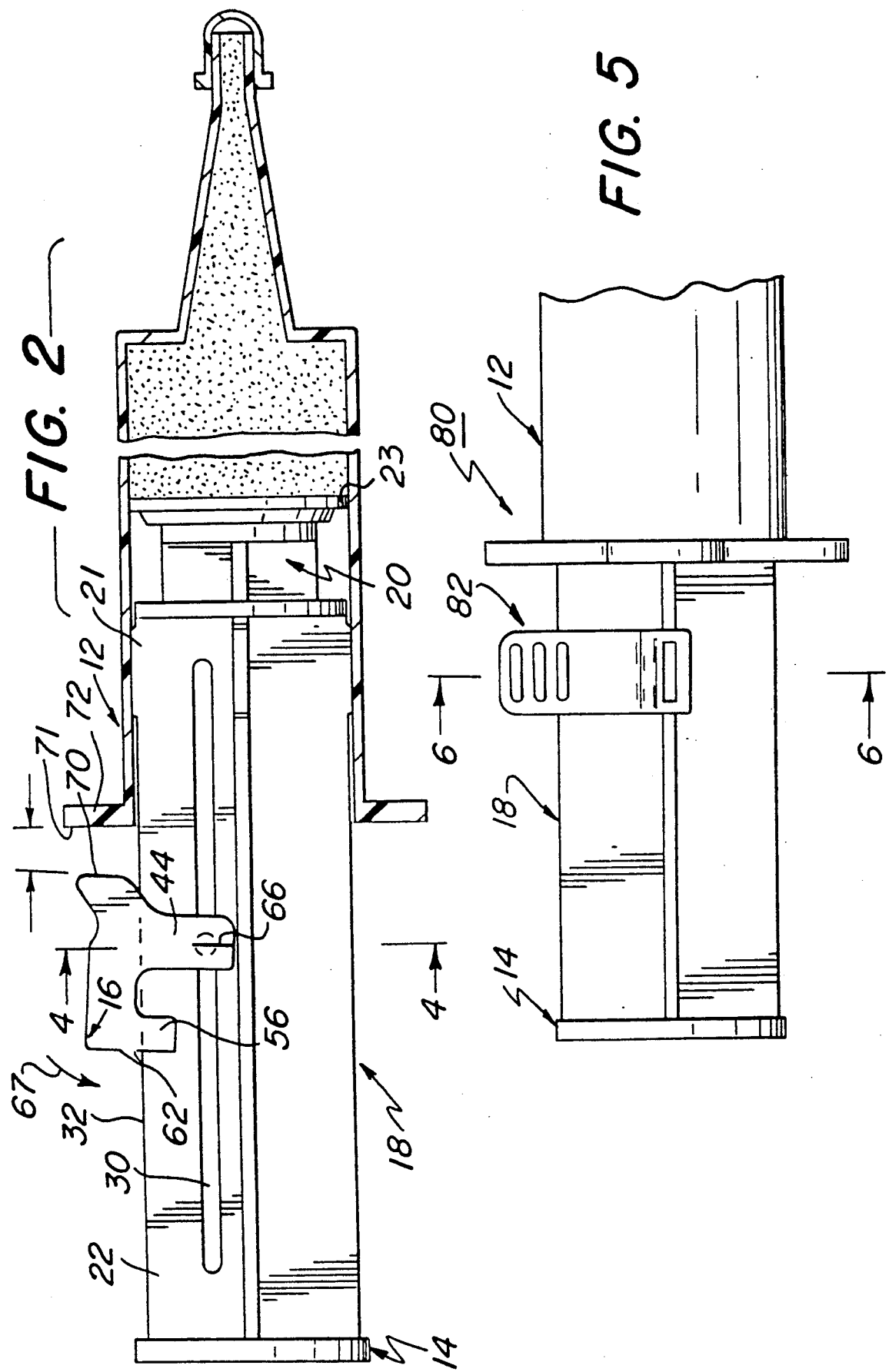

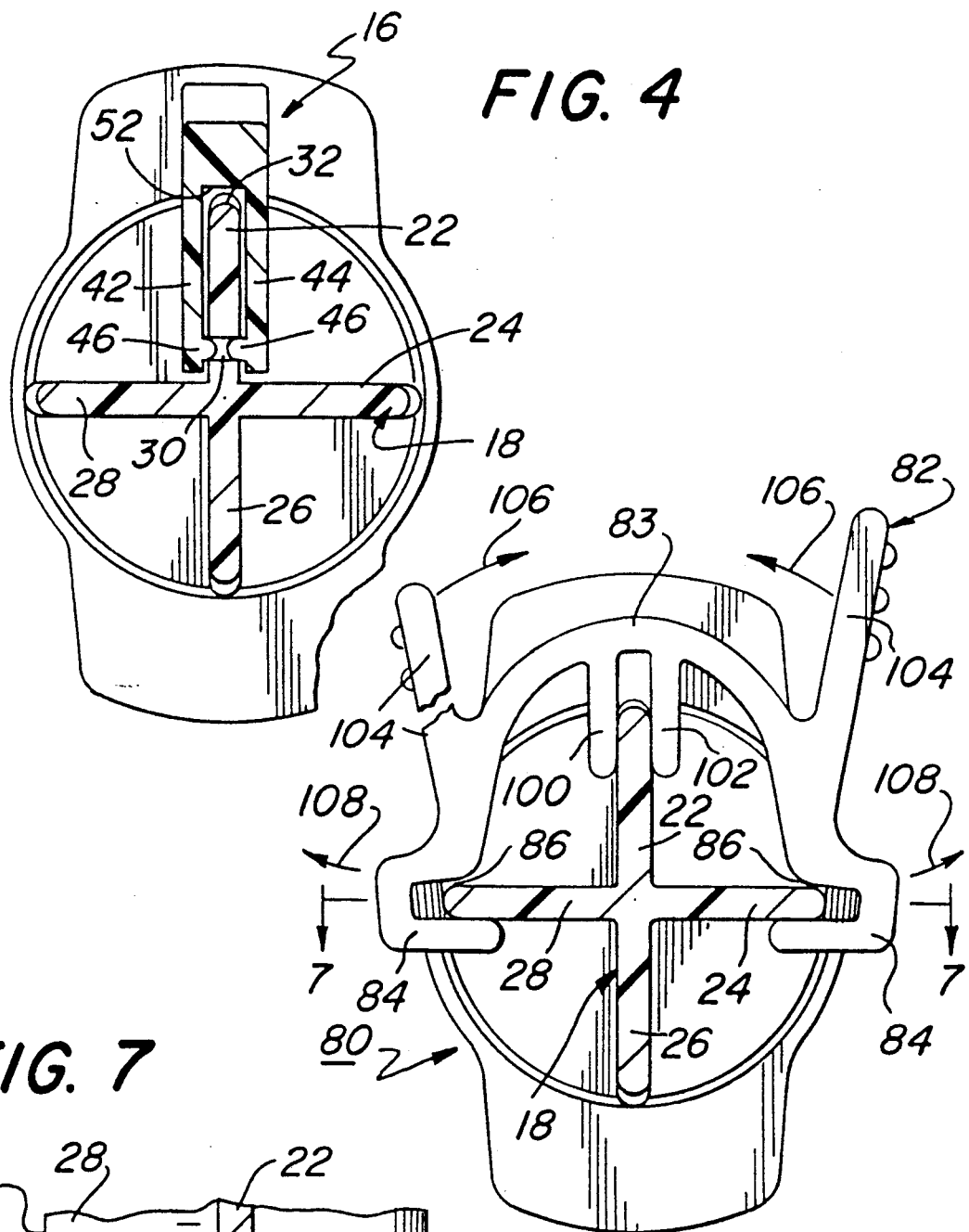

SYRINGE FOR DISPENSING MEASURED QUANTITIES OF A MATERIAL

FIELD OF THE INVENTION

This invention relates generally to syringes, and more specifically to a syringe for dispensing measured quantities of a material (e.g., a medicament) and which employs a unique arrangement for setting the desired measured quantity to be dispensed.

BACKGROUND ART

It is well known in the prior art to provide syringes with movable stop members forming a part of the plunger rod, for the purpose of permitting the setting of the desired dosage to be dispensed. These syringes are widely used in dispensing medicaments, particularly in the veterinary field.

One common prior art design for adjusting the dosage to be dispensed employs a threaded nut cooperating with threads on the exterior surface of the plunger rod to permit the nut to be adjusted along the length of the rod to a desired, spaced position from an outer marginal surface of the syringe barrel. Upon depression of the plunger rod, for the purpose of dispensing a medicament from the syringe barrel, the nut will engage the outer margin of the barrel to control the quantity of medicament dispensed from the syringe. Typical syringes employing a rotary nut are disclosed in U.S. Pat. Nos. 475,909, issued to Wilcox; 3,563,240, issued to Silver; 4,246,898, issued to Travalent et al.; 4,153,056, issued to Silver et al.; and British patent No. 1,212,823, issued to Silver.

A problem encountered in the prior art systems employing rotating nuts, other than the system described in the Silver U.S. Pat. No. 4,513,056, is that the plunger rod of the syringe must be made in two sections, in order to permit the nut to be inserted over the rod, as it cannot fit over the plunger seal at the end which is necessarily wider than the rod. This increases the manufacturing, material and assembly costs, as compared to a system in which the plunger rod and plunger seal are made as a one-piece unit. The device disclosed in the aforementioned Silver '056 patent does not suffer from this deficiency because the ring structure is of a split construction, and is designed to be inserted over the one piece plunger rod in a direction laterally of the longitudinal axis of said rod.

In the construction disclosed in the Silver '056 patent the adjustable nut can be a one-piece, hinged element having two adjacent open end portions that can be secured to each other to form a complete annular nut. Alternatively, the adjustable member can be made of two separate pieces which can be placed around the stem and fastened together. A split ring construction has proven to be not well suited for use in dispensing highly viscous, pasty substances, wherein high pressures need to be imparted to the plunger rod to dispense the substance. Under such high pressure operation the split ring pops off the plunger rod or has actually fractured when pressed against the syringe barrel.

There are several ways disclosed for adjusting the dosage to be dispensed in the dispenser described in the Silver '056 patent. One way is to rotate the nut axially along the plunger rod, through cooperating threads on the nut and the rod. In an alternative embodiment the plunger rod can have a smooth, unthreaded surface, and the nut can be engaged with the plunger rod solely by friction, in which case the nut can be slide (i.e., without rotation) along the rod to a desired location. In this latter embodiment there is no positive means for retaining the nut in its set position to prevent undesired, inadvertent displacement of the nut along the rod. An additional mode of adjusting the nut on the rod, and one which is suggested when the position of the nut on the rod is a substantial distance from its desired position, is to physically remove the split or hinged nut from the rod and replace it adjacent its desired location. This latter method of adjusting the dosage requires the disassembly and reassembly of the nut with the rod; a procedure which is somewhat complex and undesirable.

Although the use of a solid threaded nut for setting the dosage eliminates the problems encountered with the slit ring arrangement, a solid nut presents other deficiencies which increase the cost of manufacture, assembly and use of the syringe. First, if a person wants to dispense a large percentage (e.g., 50%, or even 100%) of the material in the barrel, it is necessary to rotate the nut a substantial distance alone the piston rod, from its initial position adjacent the end of the syringe barrel, where it is required to be located initially, to lock the plunger rod so that it will not inadvertently be moved to dispense the material in the barrel. Second, when the syringe barrel is prefilled in automated equipment it is necessary to rotate the nut to the upstream end of the plunger rod, adjacent the thumb pad, so that the nut will not interfere with the filling and venting of the syringe barrel. After the syringe barrel has been filled the continuous nut must be rotated in the opposite, or downstream, direction along the plunger rod, to the marginal end of the syringe body, to thereby lock the plunger rod against inadvertent movement into the syringe barrel, which, if permitted to occur, would result in the inadvertent dispensing of the material from the barrel. The need to manipulate or adjust the nut along the plunger rod, as described above adds undesired cost to the manufacturing and assembly operations.

It also has been suggested in the prior art to employ a stop member which is adapted to be slid along the length of the rod of a syringe into a desired notch in the rod, for the purpose of setting the desired dosage to be dispensed. Representative devices of this type are disclosed in U.S. Pat. Nos. 4,642,102, issued to Ohmori, and 1,852,658, issued to Kile. These devices do not permit infinite adjustment of the dosage to be dispensed, since they require the stop member to be positively located in a preformed notch.

In summary, the prior art syringes for dispensing measured quantities of a medicament generally have been considered to be unreliable in setting and maintaining the desired dosage to be dispensed, to lack the desired flexibility in adjusting the dosage within very narrow limits, to be too cumbersome to handle in assembly before and during filling of the syringe body and to be more costly to manufacture.

OBJECTS OF THE INVENTION

It is a general object of this invention to provide a syringe for dispensing a metered dosage of a material (e.g., a medicament), wherein the dosage of the material to be dispensed can be set easily and quickly.

It is a further object of this invention to provide a syringe for dispensing a metered dosage of a material, wherein the desired dosage to be dispensed is infinitely variable within finite limits.

It is a further object of this invention to provide a syringe for dispensing a metered dosage of a material, wherein the desired dosage to be dispensed can be positively set and which is not susceptible of being inadvertently changed.

It is a further object of this invention to provide a syringe for dispensing a metered dosage of a medicament, which is simple in construction, low in cost and which is made from a minimum or reduced number of parts.

It is a further object of this invention to provide a syringe which is easy to manufacture and also easy to handle during prefilling thereof, to thereby minimize the manufacturing and assembly costs thereof.

It is a further object of this invention to provide a disposable syringe which is economical to manufacture, fill and assemble.

SUMMARY OF THE INVENTION

The above and other objects of this invention are achieved in a syringe for dispensing a metered dosage of a material (e.g., a medicament) including a hollow syringe barrel for containing the material to be dispensed and having a discharge end portion and an open opposite end portion, through the which the material to be dispensed is introduced and into which a plunger rod is slidably received. The plunger rod includes a rail section and an axially adjustable stop member engaged with the rail section outside the syringe barrel to limit the linear travel of the plunger rod into the syringe barrel. As a result of this arrangement the volume of material dispensed from said syringe barrel is controlled. In accordance with this invention the axially adjustable stop member includes a knife edge for digging or embedding into a surface of the rail portion of the piston rod, to thereby positively lock the stop member in a fixed position on the rail section for limiting the axial movement of the plunger rod into the syringe barrel for dispensing the desired dosage of material.

In a preferred embodiment of this invention the axially adjustable stop member is secured to the plunger rod for both axial and pivotal movement. The pivotal movement of the stop member is relied upon to drive the knife edge thereof into the plunger rod for the purpose of positively locking the stop member in a desired, adjusted position on said rod.

In accordance with a preferred embodiment of this invention the adjustable stop member engages a surface of the syringe barrel adjacent the open end thereof when the desired dosage has been dispensed, and this engagement imparts a force on the stop member to compliment the locking action provided between the knife edge and the rod. In fact, the harder one depresses the plunger when the stop member is in engagement with the surface of the syringe barrel adjacent the open end thereof, the more deeply the knife edge of the stop member embeds into the piston rod, to thereby prevent the overriding and inadvertent dispensing of an undesired, excessive dosage.

In another embodiment of this invention the axially adjustable stop member is in the form of a clip having transversely spaced-apart marginal ends. These marginal ends include slots with knife edges therein for receiving sections of the plunger rod. The knife edges in the slots are biased in a direction to dig into or embed in confronting surfaces of the plunger rod. The clip further includes actuating means to release the engagement of the knife edges from the rod, to permit the stop member to be axially moved along the rod for setting the desired dosage to be dispensed.

In the preferred embodiments of this invention the adjustable stop member is snapped into engagement with the rod in a transverse direction (e.g., in a direction substantially 90 degrees to the direction of axial movement of the rod within the syringe barrel).

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is an isometric view of the syringe of this invention, illustrating, in phantom representation, the manner in which it is gripped for dispensing a desired dosage of material therefrom;

FIG. 2 is an enlarged sectional view taken line 2—2 of FIG. 1;

FIG. 3 is a enlarged fragmentary side elevational view, showing the cooperation among the syringe barrel, the plunger rod and the adjustable stop member, when a desired, preset dosage of material has been dispensed from the syringe;

FIG. 4 is an enlarged sectional view taken along line 4—4 of FIG. 2;

FIG. 5 is an enlarged fragmentary sectional view of the syringe, showing a modified stop member in accordance with this invention;

FIG. 6 is an enlarged sectional view taken along line 6—6 of FIG. 5; and

FIG. 7 is an enlarged sectional view taken along line 7—7 of FIG. 6.

DESCRIPTION OF THE PREFERRED EMBODIMENTS OF THE INVENTION

Referring now in greater detail to the various figures of the drawings, wherein like reference characters refer to like parts, a syringe for dispensing a metered dosage of material and embodying the present invention is generally shown at 10 in FIG. 1. The device 10 basically comprises a syringe barrel 12 having a discharge end portion through which a medicament is dispensed and an open opposite end portion through which the medicament is introduced, a plunger rod 14 inserted within the open opposite end portion of the syringe barrel for dispensing material through the discharge end portion of the syringe barrel, and an axially, infinitely adjustable stop member 16 secured to the plunger rod for positively setting the length of travel of the plunger rod to thereby control the volume of material dispensed from the syringe.

Referring specifically to FIG. 2, the plunger rod 14 preferably is a unitary molded member including a rail section 18 and a piston section 20. The piston section includes a plunger seal 23 and a radially enlarged region 21, both of which frictionally engage the inner wall of the syringe barrel 12. This enlarged region 21 stabilizes the plunger rod 14 for linear movement within the syringe barrel 12, to thereby prevent the plunger rod from tilting, which would allow leakage past the plunger seal 23.

Referring to FIGS. 2 and 4, the rail section 18 is cruciform in transverse cross-section, including four rails 22, 24, 26 and 28. An elongate slot 30 is formed through at least one of the rails (e.g., 22) in a region inwardly of the outer surface 32 thereof. As can be seen best in FIG. 2, the outer surface 32 is substantially planar (but could also be a linear edge surface), and is free of notches and/or other stop member-retaining grooves. It is this feature which permits universal, infinite adjustment of the stop member on the plunger rod 14, within the finite distance of the elongate slot 30.

Referring to FIGS. 1, 2 and 4, the axially adjustable stop member 16 is infinitely variable along the length of the rail 22 on which it is mounted, and includes transversely spaced-apart legs 42 and 44 which straddle said rail. The lower end of the legs include inwardly directed, generally spherical projections 46 (FIG. 4) which snap-fit into the elongate slot 30. In this manner the stop member 16 is firmly retained for sliding movement on the rail 22. In addition, the cooperation between the slot 30 and spherical projections 46 permits pivotal movement of the stop member on the rail to assist in locking the stop member 16 on a desired dose line of a calibrated scale, in a manner which will be described in greater detail hereinafter. However, at this point it should be noted that the recess between the transversely spaced-apart legs 42 and 44 includes a base 52 which is spaced radially outwardly of the outer surface 32 of rail 22 when the spherical projections 46 are retained within the elongate slot 30. It is this spacing that permits the pivotal movement between the stop member 16 and the rail 22 to take place.

Referring specifically to FIGS. 1 and 2, the slidable stop member 16 also includes a pair of transversely spaced-apart legs 54 and 56 at the trailing, or upstream, end thereof. These latter legs are shorter in length than the legs 42 and 44, primarily because they do not need to cooperate with the elongate slot 30. However, these transversely spaced-apart legs 54 and 56 do cooperate with the transversely spaced-apart legs 42 and 44 to stabilize the stop member on the rail 22, so that it can be smoothly and easily slid along the rail.

Still referring to FIGS. 1 and 2, the stop member 16 includes a cutting or knife edge 62 extending downwardly and rearwardly from a rear wall thereof, for embedding into the outer surface 32 of the rail. This embedding action results in the effective locking of the stop member in any desired position on the rail, within the axial confines of the slot 30. That is, the stop member 16 can be axially moved along the entire length of the elongate slot 30, and be locked in any position along its length of travel by causing the cutting edge 62 thereof to embed into the outer edge surface 32 of the rail 22.

Referring specifically to FIGS. 1-3, the stop member 16 preferably includes a generally concave groove or surface 63 in the upper surface thereof, which can be engaged by a user's thumb or finger to slide the stop member to a desired position on the rail section 18, for the purpose of setting the dosage which is to be administered from the syringe 10. To accomplish this result a volumetric scale 64 is provided on a rail 28 of the plunger rod 14, which is adjacent and at right angles to the rail upon which the stop member 16 is mounted. An indicator line 66 is provided on each of the transversely spaced-apart legs 42 and 44 of the stop member 16, for the purpose of permitting the setting of the stop member on the proper dose line of the volumetric scale to dispense a desired volume of material from the syringe.

After the stop member 16 has been slid to the desired position on the rail, the rear or upstream end of the stop member can be manually pressed downwardly, in the direction indicated by arrow 67 in FIG. 2, to force the cutting edge 62 to embed into the upper surface of the rail. This action locks the stop member in proper position on the rail section 18 of the plunger rod 14.

After the stop member 16 has been set to permit the syringe to dispense a desired dosage, as is illustrated in FIGS. 1 and 2, the thumb pad of plunger 14 is pressed axially inwardly in a downstream direction, as is indicated by arrow 68 in FIG. 3, to dispense the desired volume of material.

Referring specifically to FIGS. 2 and 3, the stop member 16 includes a wall section 70 at the downstream end thereof for engaging the generally planar surface 71 of the annular flange 72 located at the open upstream end of the syringe barrel 12, when the plunger rod 14 has been moved the precise distance for dispensing the desired volume of material from the syringe. In view of the fact that the wall section 70 of the stop member 16 engages planar surface 71 of the syringe barrel 12 in a region radially outwardly of the pivot axis for the stop member 16, the force imposed upon the stop member by this engagement will cause the stop member to rotate in the general direction indicated by arrow 74. This rotational movement causes the upstream or rear end of the stop member to move downwardly in the general direction of arrow 75, to enhance the locking action provided by the cutting edge 62 embedding into the outer surface 32 of the rail 22. In other words, the force imposed upon the stop member 16 at a point in time when the desired volume of material has been dispensed is in a direction to compliment the locking action between the stop member 16 and the rail section 18 of the plunger rod 14. This is an extremely important and desirable feature in the present invention, since it prevents the inadvertent unlocking of the stop member from the rail section 18, which, if permitted to occur, could result in the dispensing of an undesired dosage from the syringe.

When it is desired to reset the stop member 16 after its first use, for the purpose of dispensing a second desired dosage, the stop member 16 is pushed at groove 63 to cause a slight clockwise rotation of the stop member, as viewed in FIGS. 2 and 3, to disengage the cutting edge 62 from the rail 22. The limited area of contact between the wall section 70 and the surface 71 of the annular flange 72 permits this slight clockwise rotation to take place without the need to first physically pull back the plunger to disengage the surface 70 from the surface 71 of the annular flange 72.

Referring to FIGS. 5-7, an alternative embodiment of the syringe is generally shown at 80. This syringe is virtually identical to the syringe 10 discussed above, except for the construction of the axially moveable stop member 82, and the fact that the elongate slot 30 for cooperating with the stop member 16 in the syringe 10 is not required for cooperating with the stop member 82 employed in the syringe 80.

Still referring to FIGS. 5-7, the stop member 82 is a resilient clip member having a generally U-shaped barrel section 83 with the marginal ends 84 thereof defining slots 86 facing inwardly for receiving the marginal ends of diametrically opposed rails (e.g., 24 and 28) therein.

The stop member 82 has a smaller linear dimension than the stop member 16 employed in the earlier described embodiment of the invention. This shorter linear dimension permits the stop member 82 to be used with a standard length plunger. The greater linear dimension of the stop member 16 may require the plunger employed with the syringe to be of a custom size.

The clip member 82 further includes integrally molded knife edges 90 within the slots 86. Moreover, the clip member is molded so that the marginal ends 84 are normally biased inwardly toward each other to cause the knife edges 90 to embed in the outer marginal surfaces 32 of the arms 24 and 28, as can be seen best in FIG. 7. As a result of this arrangement the stop member 82 is automatically locked to the rail section 18 of the plunger rod 14, to thereby prevent linear movement of the stop member along the plunger rod.

Still referring to FIG. 7, a volumetric scale 64 is provided on a planar surface of the rail 28, in the same manner as described earlier in connection with the syringe 10. However, in the syringe 80 either the upstream or downstream marginal wall of the clip member 82 constitutes the indicator surface which is to be aligned with the desired volume indicator line of the volumetric scale 64.

Referring specifically to FIG. 6, the clip member 82 further includes inwardly directed ribs or arms 100, 102 at the base of the U-shape barrel section 83 thereof, to thereby straddle and slidably engage the rail 22 of the rail section 18. The clip member 82 further includes outwardly directed actuating arms 104 which, when biased in an inward direction as indicated by the arrows 106, force the marginal ends 84 of the clip member outwardly, in the direction of arrow 108, to thereby release the embedded engagement between knife edges 90 and the outer surfaces 32 of the rails 24 and 28. This permits the clip member 82 to be slid along the rail section 18 to any desired position, for controlling the volume of material to be dispensed from the syringe. Alternatively, if desired, the actuating arms 104 can be sufficiently biased to actually permit the clip member 82 to be physically removed from the rail section 18, and thereafter relocated in a different area of the rod for the purpose of resetting the dosage to be dispensed or locking the plunger against movement in a direction into the syringe barrel. This permits the rapid setting of the stop member 82, in the same manner as the stop member 16, for either partially or totally emptying the syringe.

Another very important benefit of the alternative embodiment 80—like the embodiment 16—is that the stop member 82 can be attached to the plunger rod 14 after the syringe barrel 12 has been filled and the plunger rod inserted therein. This permits the economy of molding an all one-piece plunger and rod and allowing for the installation of same after filling the syringe, thus not interfering with automatic equipment handling of the product.

There are a variety of modifications which can be made to the syringes 10 and 80 within the scope of this invention. For example, although indicator lines 66 preferably are provided on both of the legs 42 and 44 of the stop member 16, it is within the scope of this invention to include the indicator line on only one leg, or alternatively, to employ one of the exposed marginal surfaces of the stop member as an indicator surface to be aligned with the volumetric scale 64. Also, the specific location of the volumetric scale on the rail section 18 may be varied. The important criteria is that an indicator line or surface of the stop member be alignable with the dose lines on the volumetric scale, to thereby set the desired dosage to be dispensed.

In connection with the syringe 80 the preferred clip member 82 includes a pair of axially spaced-apart knife edges 90 associated with each of the slots 86 (FIG. 7). However, if desired, the number and arrangement of these cutting edges may be varied.

One of the important aspects of this invention is that the stop members 16 and 82 are provided with cutting edges for embedding into a surface of a rail of the plunger rod 14. To this end the stop members preferably are molded from a harder plastic material than that which is employed to fabricate the rail section 18 of the plunger rod 14. For example, the stop members 16 and 82 can be molded of a hard plastic, such as Nylon or Deldrin, whereas the rail section 18 of the plunger rod 14 can be molded of a softer polymer, such as high or low density polyethylene. The specific plastics employed to fabricate the syringes 10 and 80 are not considered limitations on the present invention. However, in accordance with a preferred embodiment of the invention the important factor is that the plastic material employed to form the stop members 16 and 82 be harder than the plastic material employed to form the rail section 18 in the syringes 10 and 80. If desired, the knife edge may be provided on a separate metal member, in which case the plastic employed to form the rail section 18 need only be soft enough to permit the metal knife edge to embed therein.

Without further elaboration, the foregoing will so fully illustrate my invention that others may, by applying current or future knowledge, adopt the same for use under various conditions of service.

I claim:

1. A syringe for dispensing a predetermined dosage of material, said syringe comprising a hollow syringe barrel having a discharge end for the material to be dispensed and an open, opposite end, a plunger rod slidably received in said syringe barrel through said open, opposite end, said plunger rod having a first end portion located within said syringe barrel and a rail section having at least a portion thereof located outside of said syringe body, said plunger rod being movable in a downstream direction into said syringe barrel for dispensing a material through the discharge end of said syringe barrel, a stop member attached to the rail section in a region outside of said syringe barrel and being axially movable along the length of the rail section to set the length of travel of the plunger rod in said downstream direction for controlling the volume of material to be dispensed, characterized in that the stop member includes a knife edge for embedding into the rail section to lock the stop member in any one of an infinite number of desired positions on said rail section.

2. The syringe of claim 1, characterized in that both the rail section of the plunger rod and the stop member are made from plastics materials, the plastics material of the rail section being softer than the plastics material of the stop member.

3. The syringe of claim 1, characterized in that the stop member includes a downstream surface for engaging a surface of the syringe barrel at the open end of said barrel when the plunger rod has been moved in a downstream direction to dispense a desired volume of material, said knife edge being located at an upstream end of the stop member and the stop member being pivotally secured to the plunger rod, whereby engagement of the downstream surface of the stop member with the surface of the syringe barrel at the open end of said barrel forces the stop member to pivot in a direction for causing the knife edge to embed into the rail section of the plunger rod.

4. The syringe of claim 1, characterized in that the rail section includes at least one rail, said stop member being slidably and pivotally attached to a rail for permitting linear movement of the stop member along said rail, and pivotal movement of the stop member relative to said rail for aiding in embedding the knife edge of the stop member into a surface of said rail.

5. The syringe of claim 4, characterized in that the rail includes an elongated opening therein, said stop member including leg means for straddling said rail, and projection means on said leg means for engaging within said elongated opening, whereby said stop means is linearly movable within the confines of said elongated opening and is pivotally secured to said rail within said opening by said projection means.

6. The syringe of claim 5, characterized in that the stop member includes a downstream surface for engaging a surface of the syringe barrel at the open end of said syringe barrel when the plunger rod has been moved in a downstream direction to dispense a desired volume of material, said knife edge being located at an upstream end of the stop member and the stop member being pivotally secured to the plunger rod, whereby engagement of the downstream surface of the stop member with the surface of the syringe barrel at the open end of said barrel forces the stop member to pivot in a direction for causing the knife edge to embed into the rail section of the plunger rod.

7. The syringe of claim 1, characterized in that said rail section includes a volumetric scale thereon and said stop member includes and indicator means for cooperating with the volumetric scale for permitting the stop member to be locked on the rail section in a location for dispensing a desired volume of material.

8. The syringe of claim 7, characterized in that the rail section is cruciform in cross-section and includes four rails, each rail being disposed at an angle of ninety degrees from each adjacent rail, said stop member being slidable on one of said rails and said volumetric scale being included on a rail adjacent the rail on which the stop member is slidable.

9. The syringe of claim 8, characterized in that the stop member is both slidable and pivotal on the rail.

10. The syringe of claim 1, characterized in that said stop member is a resilient clip having spaced apart marginal edges with slots therein for receiving sections of the rail section therein, said slots including knife edges therein for embedding in sections of the rail section received within the slots.

11. The syringe of claim 10, characterized in that said rail section is cruciform in cross-section and includes four rails, each rail being disposed at an angle of ninety degrees from each adjacent rail, said slots being diametrically opposed to each other for receiving rails which are diametrically opposed to each other, said knife edges being located at the bases of the slots for embedding in outer exposed surfaces of said diametrically opposed rails.

12. The syringe of claim 11, characterized in that a pair of knife edges are located at the base of each slot, said knife edges in each slot being spaced-apart from each other in the axial direction of movement of the plunger rod.

13. The syringe of claim 10, characterized in that the spaced-apart marginal edges are normally biased toward each other to move the knife edges into embedded engagement with the rail section, to thereby lock the clip member to the rail section for preventing axial movement of the clip member relative to the rail section.

14. The syringe of claim 13, characterized in that said resilient clip includes actuating arm means for biasing the spaced apart marginal edges away from each other to move the knife edges out of embedded engagement with the rail section, to thereby permit the resilient clip member to be moved relative to the rail section.

15. The syringe of claim 14, characterized in that said rail section is cruciform in cross-section and includes four rails, each rail being disposed at an angle of ninety degrees from each adjacent rail, said slots being diametrically opposed to each other for receiving rails which are diametrically opposed to each other, said knife edges being located at the bases of the slots for embedding into outer exposed surfaces of said diametrically opposed rails.

16. A syringe for dispensing a predetermined dosage of material comprising hollow barrel means having a discharge end from which the material can be dispensed and an open, opposite end, plunger means slidably received in said barrel means through said open, opposite end, said plunger means including a rail section having at least a portion thereof located outside of said barrel means, said plunger means being movable in a downstream direction into said barrel means for dispensing the material; stop means mounted for movement along the length of said rail section engageable by said barrel means to establish the length of travel of said plunger means in said downstream direction for controlling the volume of material to be dispensed, said stop means being selectively fixedly engageable with said rail section at any one of an infinite number of desired positions to lock said stop means in a desired position on said rail section.

17. A syringe as set forth in claim 16
wherein said stop means includes a knife edge selectively movable between a first position disengaged from said rail section and a second position embedded into said rail section at a precise desired location therealong.

18. A syringe as set forth in claim 16
wherein said knife edge is composed of a material which is harder than that of said rail section.

19. A syringe as set forth in claim 16 including:
indicia means on said rail section for indicating a volume of the material to be dispensed at each selected location at which said stop means is fixedly engaged with said rail section.

* * * * *